(12) United States Patent
Reiley et al.

(10) Patent No.: US 7,081,122 B1
(45) Date of Patent: Jul. 25, 2006

(54) HAND-HELD INSTRUMENTS THAT ACCESS INTERIOR BODY REGIONS

(75) Inventors: Mark A Reiley, Piedmont, CA (US); Michael L Reo, Redwood City, CA (US); Robert M Scribner, Los Altos, CA (US)

(73) Assignee: Kyphon Inc., Sunnyvale, CA (US)

( * ) Notice: Subject to any disclaimer, the term of this patent is extended or adjusted under 35 U.S.C. 154(b) by 0 days.

(21) Appl. No.: 09/421,635

(22) Filed: Oct. 19, 1999

(51) Int. Cl.
*A61B 17/34* (2006.01)

(52) U.S. Cl. .................. 606/185; 604/164.01
(58) Field of Classification Search ............ 606/1, 606/184, 185, 167, 170; 604/164.01, 164.06, 604/164.07, 264, 199, 158, 165.02, 165.04, 604/117, 164.04, 272, 111, 19, 22, 93.01, 604/164.09, 164.11, 165.01; 422/57, 58, 422/55; 600/562, 564–567
See application file for complete search history.

(56) References Cited

U.S. PATENT DOCUMENTS

| | | | |
|---|---|---|---|
| 931,327 | A | 8/1909 | Manzel |
| 2,198,666 | A | 4/1940 | Gruskin |
| D149,843 | S | 6/1948 | Ruger |
| 2,709,600 | A | 5/1955 | Lehde |
| 2,919,692 | A * | 1/1960 | Ackermann |
| 3,258,312 | A * | 6/1966 | Olson .............................. 436/1 |
| 3,523,011 | A * | 8/1970 | Bhiwandker et al. .......... 422/57 |
| 3,628,524 | A * | 12/1971 | Jamshidi |
| 3,943,932 | A * | 3/1976 | Woo ............................ 606/189 |
| 4,013,080 | A | 3/1977 | Froning |
| 4,187,607 | A | 2/1980 | Simuro et al. |
| 4,262,676 | A | 4/1981 | Jamshidi |
| 4,487,209 | A * | 12/1984 | Mehl ........................... 128/754 |
| 4,630,616 | A * | 12/1986 | Tretinyak .................... 600/566 |
| 4,793,363 | A | 12/1988 | Ausherman et al. |
| 4,820,755 | A * | 4/1989 | Webster ........................ 524/88 |
| 4,838,282 | A * | 6/1989 | Strasser et al. .............. 600/567 |
| 4,938,743 | A | 7/1990 | Lee |
| 4,967,435 | A | 11/1990 | Seals |
| 4,995,872 | A | 2/1991 | Ferrara |
| 5,086,674 | A | 2/1992 | Her |
| 5,178,267 | A | 1/1993 | Grabenkort et al. |
| 5,257,632 | A * | 11/1993 | Turkel et al. ................ 600/567 |
| 5,368,046 | A | 11/1994 | Scarfone et al. |
| 5,385,151 | A * | 1/1995 | Scarfone et al. ............ 600/567 |
| 5,385,561 | A * | 1/1995 | Cerny ........................ 604/264 |
| D358,645 | S | 5/1995 | Ryan et al. |
| 5,423,824 | A | 6/1995 | Akerfeldt et al. |
| 5,480,166 | A | 1/1996 | Milsop |
| 5,480,389 | A * | 1/1996 | McWha et al. ......... 604/165.02 |
| 5,494,382 | A | 2/1996 | Kloppers |

(Continued)

FOREIGN PATENT DOCUMENTS

EP 0 535 974 A1 * 4/1993

(Continued)

*Primary Examiner*—Nicholas D. Lucchesi
*Assistant Examiner*—A. A.
(74) *Attorney, Agent, or Firm*—Ryan Kromholz & Manion, S.C.

(57) ABSTRACT

A composite instrument is provided comprising a first functional instrument and a second functional instrument when the first functional instrument is coupled with the second functional instrument. A composite handle for the composite instrument is provided comprising a first handle and a second handle when the first handle is coupled with the second handle. The handle makes possible the reliable transmission, with increased mechanical advantage, of both torsional and longitudinal loads by the physician to the composite instrument, while resisting relative rotation between the first and second instruments. The instrument is sterilization sensitive, changing physical appearance after sterilization.

9 Claims, 14 Drawing Sheets

U.S. PATENT DOCUMENTS

| | | |
|---|---|---|
| 5,522,398 A | 6/1996 | Goldenberg et al. |
| 5,538,009 A * | 7/1996 | Byrne et al. ................. 600/567 |
| 5,575,794 A | 11/1996 | Walus et al. |
| 5,762,639 A | 6/1998 | Gibbs |
| 5,772,678 A | 6/1998 | Thomason et al. |
| 5,807,275 A * | 9/1998 | Jamshidi .................... 600/567 |
| 5,810,866 A | 9/1998 | Yoon |
| 5,843,001 A * | 12/1998 | Goldenberg ................. 600/567 |
| 5,910,197 A | 6/1999 | Caconas |
| 5,943,924 A | 8/1999 | Jarvis |
| D439,980 S | 4/2001 | Reiley et al. |
| 6,221,029 B1 * | 4/2001 | Mathis et al. ............... 600/564 |
| D449,691 S | 10/2001 | Reiley et al. |
| 6,575,919 B1 * | 6/2003 | Reiley et al. ............... 600/567 |

FOREIGN PATENT DOCUMENTS

| | | |
|---|---|---|
| EP | 0 591 851 | 4/1994 |
| GB | 2 243 788 | 11/1991 |
| WO | WO 99/37212 | 7/1999 |
| WO | WO 01/28439 | 4/2001 |

* cited by examiner

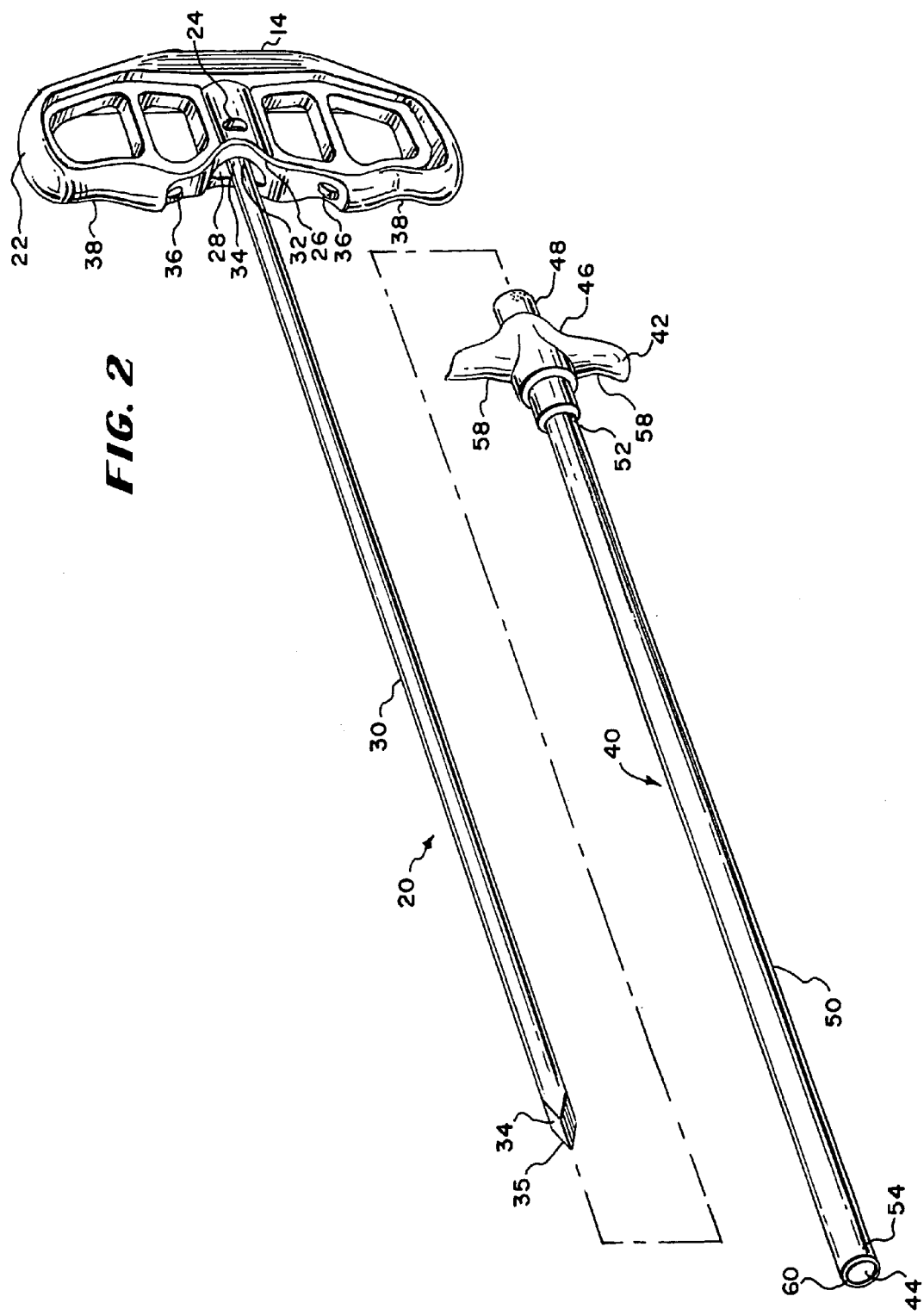

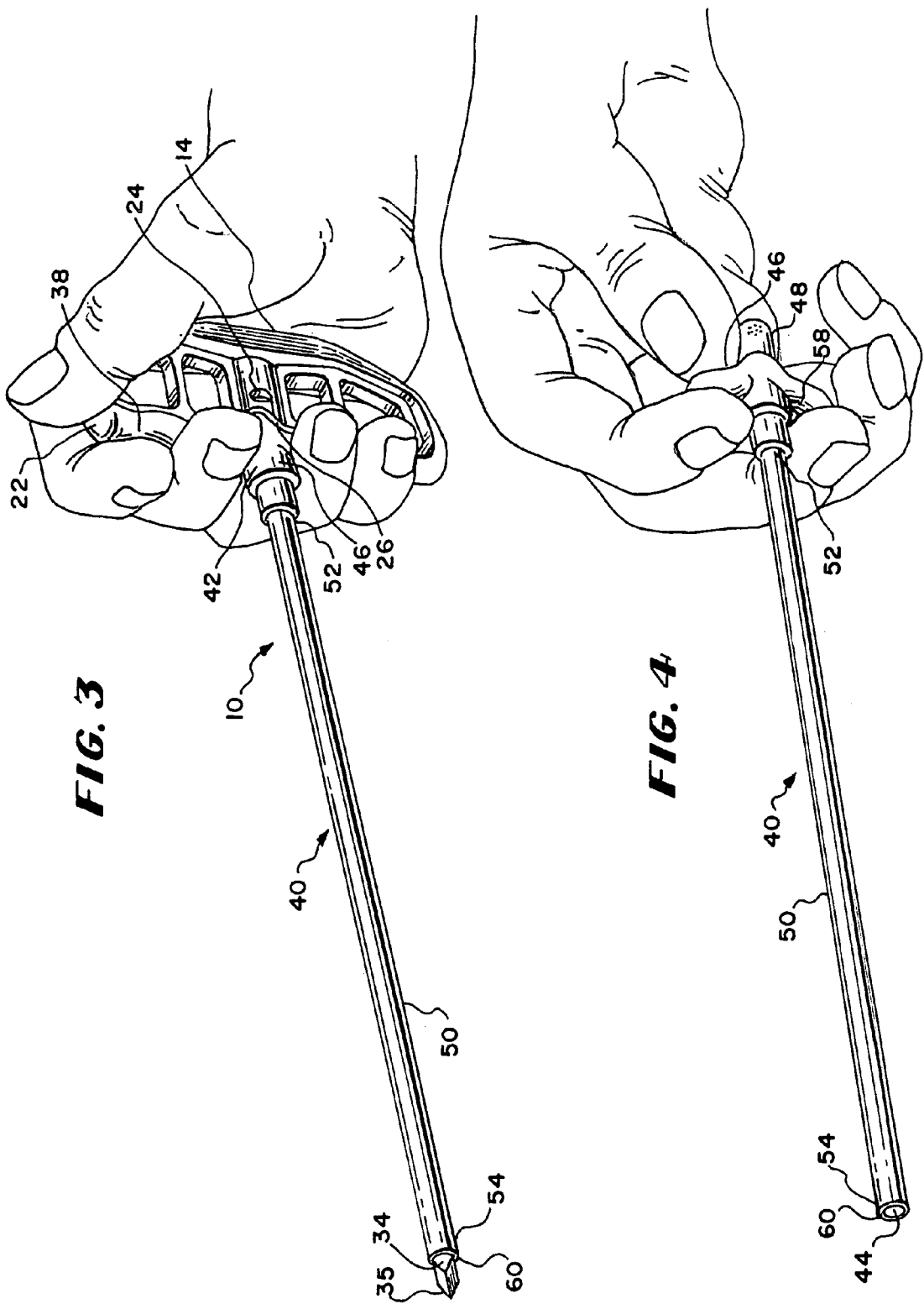

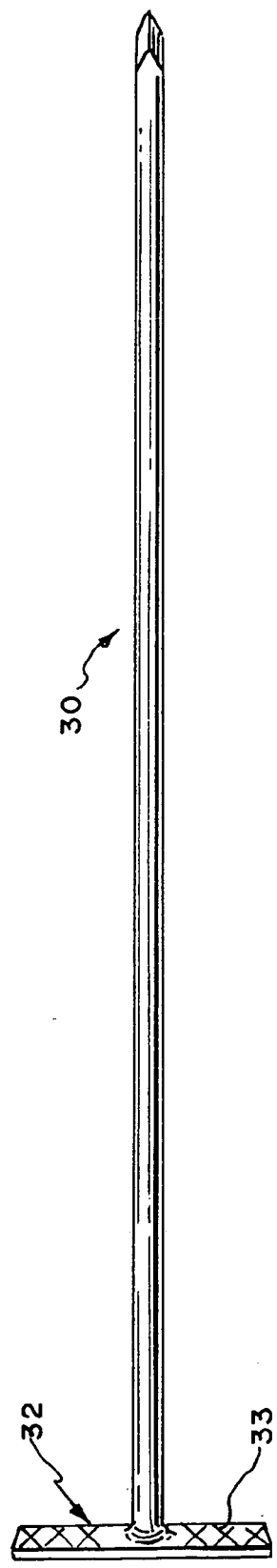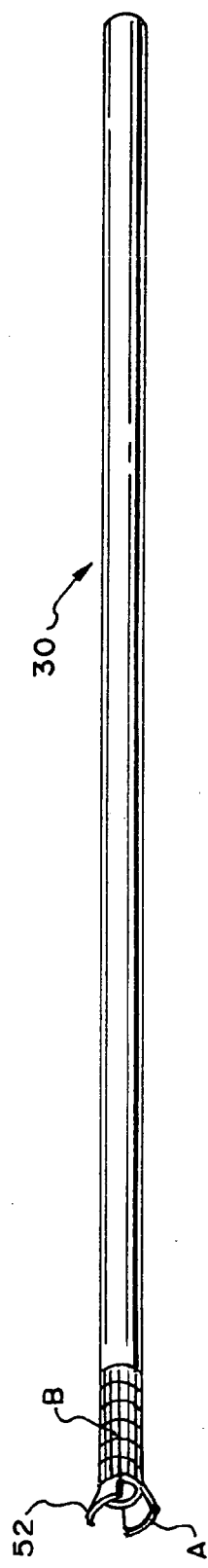

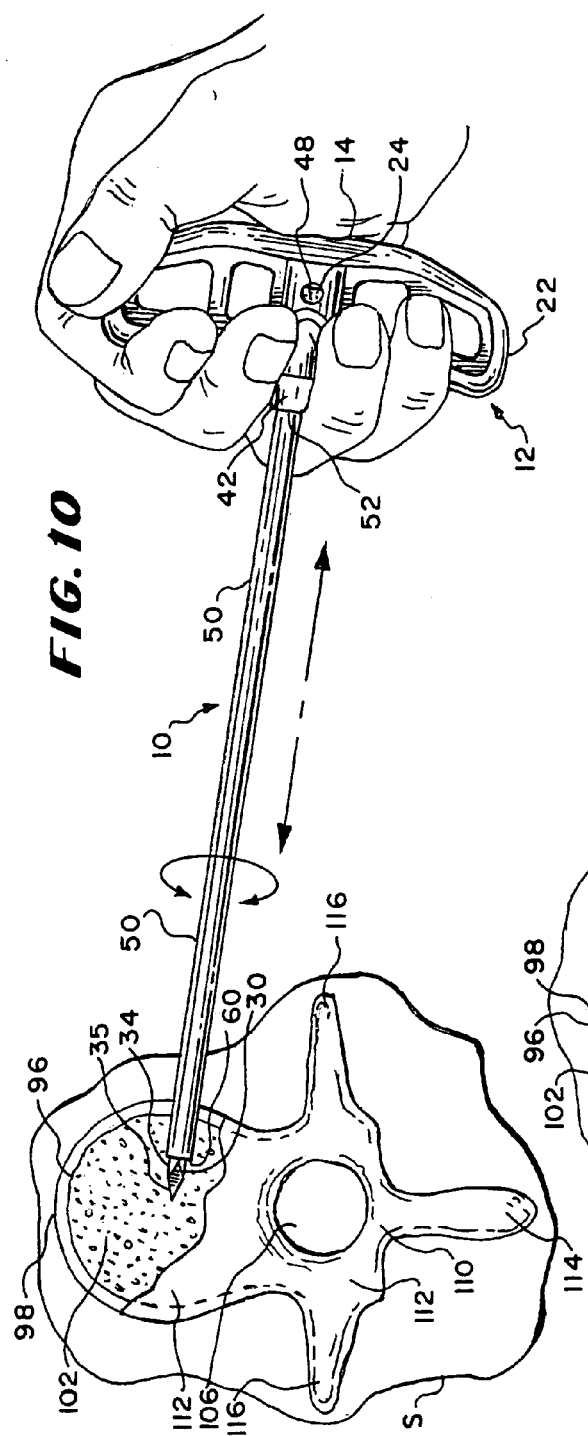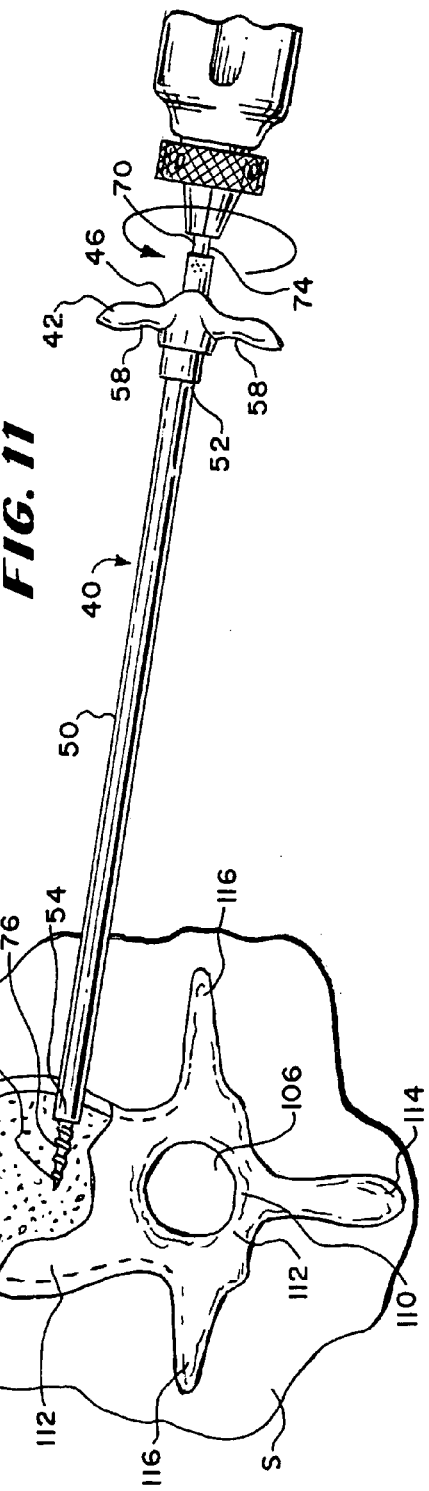

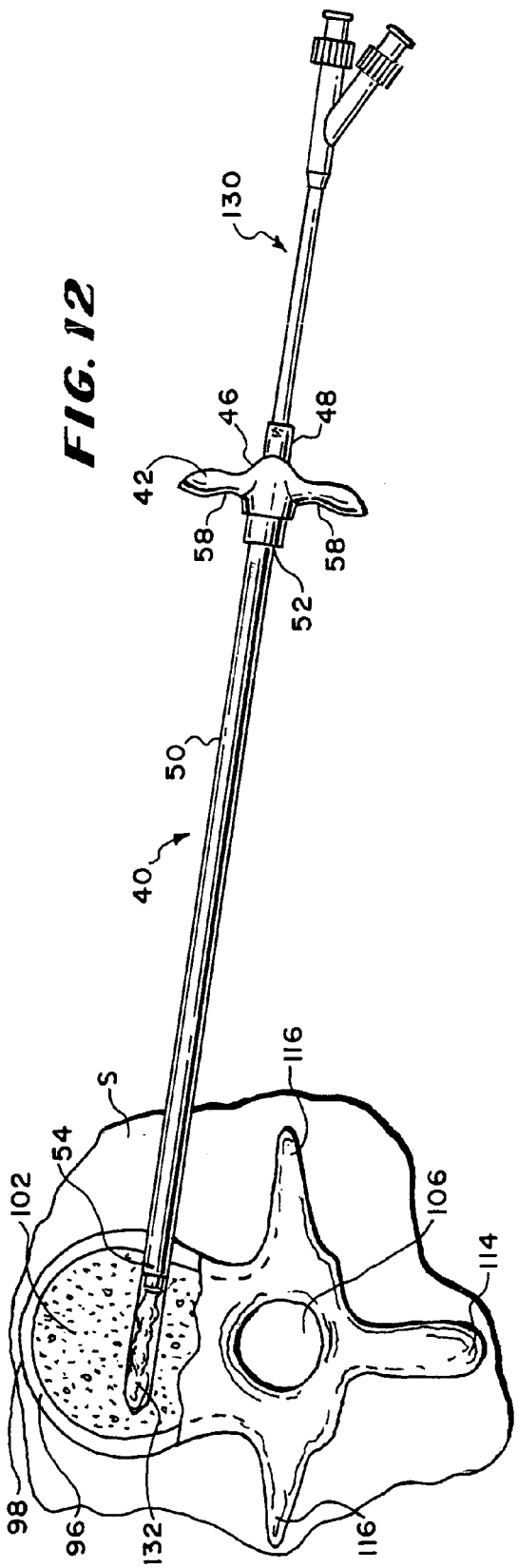

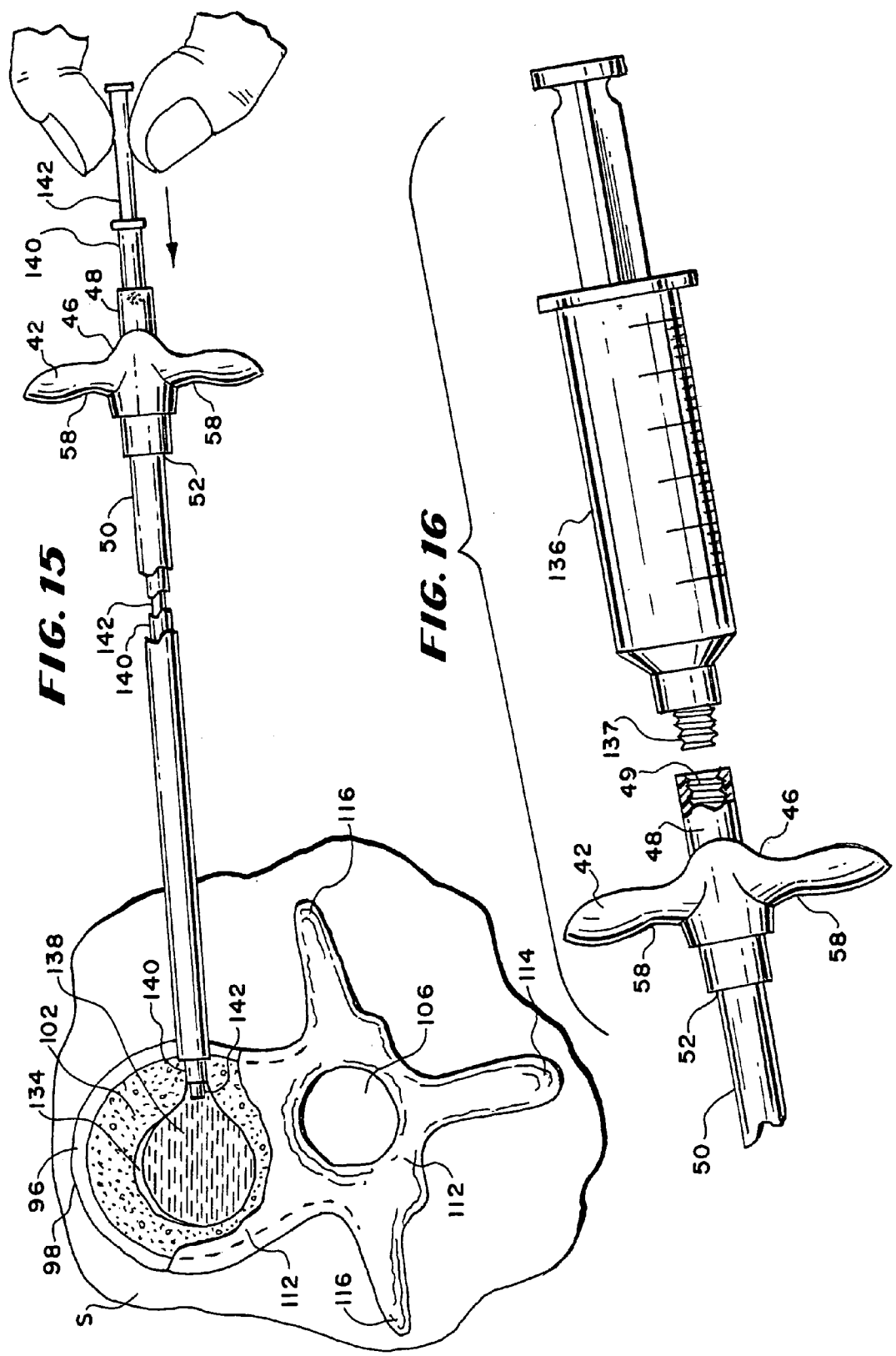

HAND-HELD INSTRUMENTS THAT ACCESS INTERIOR BODY REGIONS

FIELD OF THE INVENTION

The invention generally relates to hand-held tools and instruments and to procedures that deploy these instruments through tissue to access interior regions of the body.

BACKGROUND OF THE INVENTION

There are many different types and styles of hand-held surgical instruments that physicians use to gain access into interior body regions. These instruments are intended to penetrate tissue by the application of pushing forces, twisting forces, or both in combination.

Often, a single surgical procedure will require the physician to employ different surgical instruments, each possessing a different shape, size, and function. Often, the procedure will require the physician to deploy these instruments in both soft and hard tissue to meet the diagnostic or therapeutic objectives of the procedure. The physician will often need an enhanced mechanical advantage to advance an instrument through tissue, particularly through dense or hard tissue, such as bone.

The common need to use different instruments in a given procedure, coupled with the need to accurately and reliably deploy each of these different instruments through both soft and hard tissue, often with an enhanced mechanical advantage, complicate the physician's already difficult task. The need to handle different instruments in different ways for different purposes can distract the physician and lead to wasted effort, which can lengthen the overall time of the procedure.

SUMMARY OF THE INVENTION

The invention provides a surgical instrument with a handle design that allows initial placement of both a cannula and a trocar into interior body regions, and allows for later withdrawal of the trocar while leaving the cannula in place. The invention obviates the need for several instruments during surgical procedures, and simplifies interior access protocol. At the same time, the handle of the surgical instrument makes possible the reliable transmission, with increased mechanical advantage, of both torsional and longitudinal loads by the physician to the selected instrument.

One aspect of the invention provides a tool comprising a first functional instrument having a first handle and a second functional instrument having a second handle. The first functional instrument engages the second functional instrument, forming a composite instrument. The first handle mates with the second handle, forming a composite handle for the composite instrument.

Features and advantages of the inventions are set forth in the following Description and Drawings, as well as in the appended Claims.

BRIEF DESCRIPTION OF THE DRAWINGS

FIG. 2 is a perspective view of the first instrument separated from the second instrument;

FIG. 3 is a perspective view of a hand engaging the composite handle of the tool shown in FIG. 1;

FIG. 4 is a perspective view of a hand engaging the handle of the second functional instrument when separated from the first functional instrument;

FIG. 6C is a side view of a trocar suited for use with the composite handle of FIG. 6B;

FIG. 6D is a side view of a cannula suited for use with the composite handle of FIG. 6B;

FIG. 10 is a top view showing deployment of the composite instrument in a vertebral body, by using the composite handle to apply an axial and/or torsional force;

FIG. 11 is a top view of the vertebral body, showing deployment of a drill bit through a cannula instrument, which forms a part of the composite tool shown in FIG. 9;

FIG. 12 is a top view of the vertebral body showing deployment of an expandable structure in a collapsed condition through the cannula instrument that forms a part of the composite tool shown in FIG. 9;

FIG. 13 is a top view of the vertebral body after the structure shown in FIG. 12 is expanded to compact cancellous bone and form a cavity;

FIG. 15 is a side view showing advancement of a tamping instrument in the cannula instrument to displace and distribute material from the cannula instrument into the cavity shown in FIG. 13;

FIG. 16 is a side view of a syringe attached to the cannula instrument that forms a part of the composite tool shown in FIG. 9, for the purpose of conveying material through the cannula instrument into bone.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification describes new instruments for penetrating tissue. This specification also describes systems and methods to treat bones using expandable bodies in conjunction with new instruments for penetrating tissue.

The use of expandable bodies to treat bones is generally disclosed in U.S. Pat. Nos. 4,969,888 and 5,108,404, which are incorporated herein by reference. Improvements in this regard are disclosed in U.S. patent application Ser. No. 08/188,224, filed Jan. 26, 1994; U.S. patent application Ser. No. 08/485,394, filed Jun. 7, 1995; and U.S. patent application Ser. No. 08/659,678, filed Jun. 5, 1996, which are each incorporated herein by reference.

The new instruments, systems and methods will be described with regard to the treatment of vertebral bodies. It should be appreciated, however, that the handle configuration, instruments, systems and methods so described are not limited in their application to vertebrae. The systems and methods are applicable to the treatment of diverse bone types. Additionally, the handle configuration could be used with instruments other than a trocar and a cannula.

I. The Instruments

Figure 1:
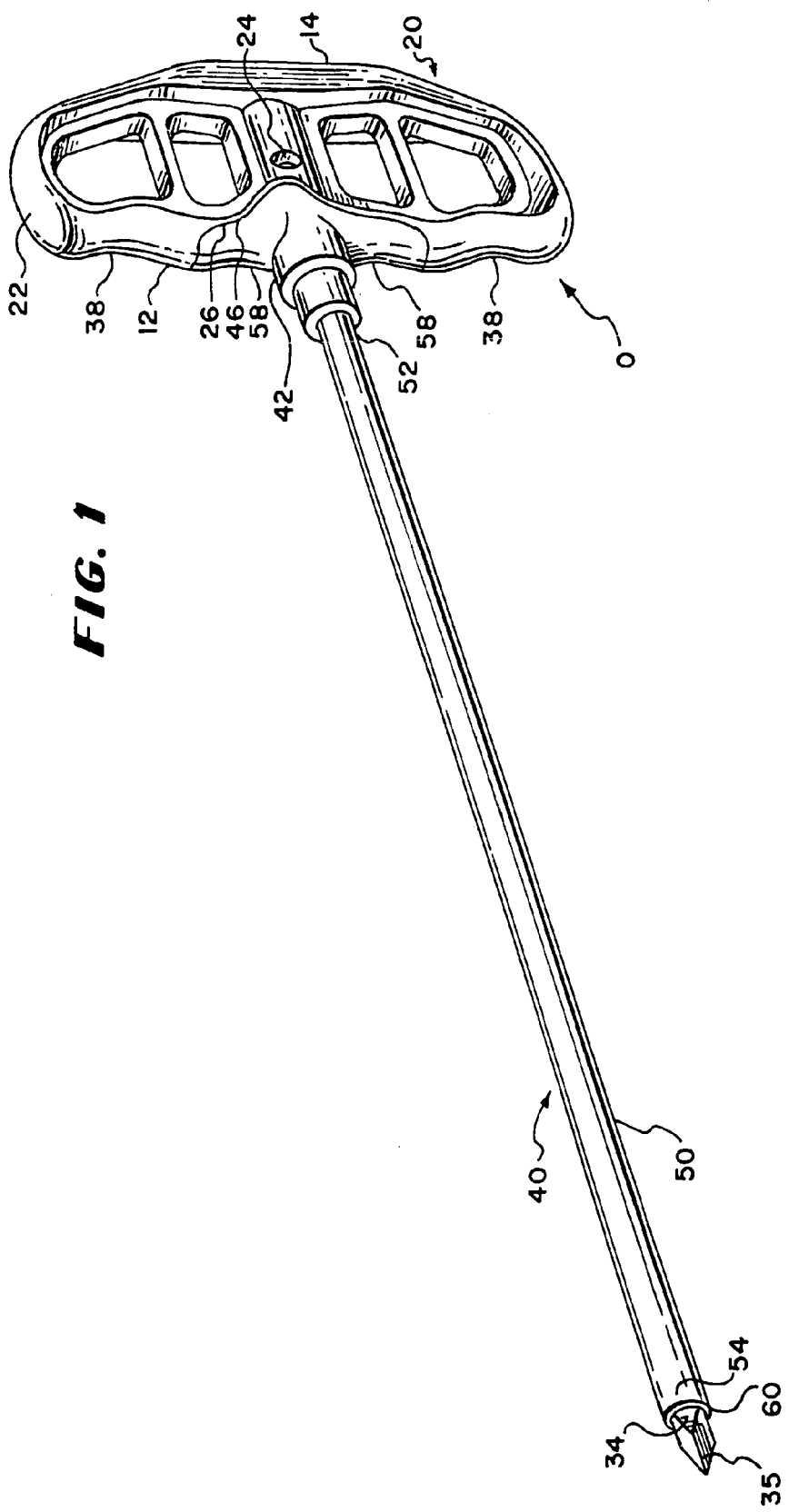
FIG. 1 is a perspective view of a first functional instrument engaging a second functional instrument to form a composite tool having a composite handle that the handles of the first and second instruments form.

FIG. 1 shows a composite instrument 10 for penetrating tissue. The composite instrument 10 includes a first functional instrument 20 and a second functional instrument 40, and a composite handle 12 comprising a first handle 22 and a second handle 42. The composite handle 12 aids a physician in manipulating the composite instrument 10, but a physician can also desirably use the first handle 22 to independently manipulate the first instrument 20 or the second handle 42 to independently manipulate the second instrument 40 during use.

The number and type of instruments 20 and 40 can vary. FIG. 1 shows two representative instruments 20 and 40, each having a different size and function. In a preferred embodiment, the first functional instrument 20 is a trocar instrument, and the second functional instrument 40 is a cannula instrument.

A. The Trocar Instrument

Referring to FIGS. 1–4, the first instrument 20 functions as a trocar instrument to penetrate tissue. A trocar 30 has a proximal end 32 and a distal end 34. The distal end 34 is tapered to present a penetrating surface 35. In use, the penetrating surface 35 is intended to penetrate soft tissue and/or bone in response to pushing and/or twisting forces applied by the physician at the first handle 22, or the composite handle 12.

The first handle 22 is coupled to the trocar 30 at the proximal end of the trocar 32. As best seen in FIG. 6C, the proximal end 32 of the trocar 30 can be formed in a T-shape, with the first handle 22 being molded around the T-shaped end. This arrangement significantly increases the mechanical strength of the bond between the handle 22 and the trocar 30, and allows significant longitudinal and torsional forces to be transmitted from the handle 22 to the trocar 30 without bond failure. Alternatively, with or without a T-shaped end, the proximal end 32 of the trocar 30 can be scored (indicated by scored region 33 in FIG. 6C) to increase the mechanical strength of the bond between the trocar 30 and the handle 22, or various bonding adhesives could be used, with varying results.

The first handle 22 desirably includes a viewing window 24, an alignment ridge receiver 26, a handle bore receiver 28, and a handle key 36, the uses of which are described later.

Figure 18:
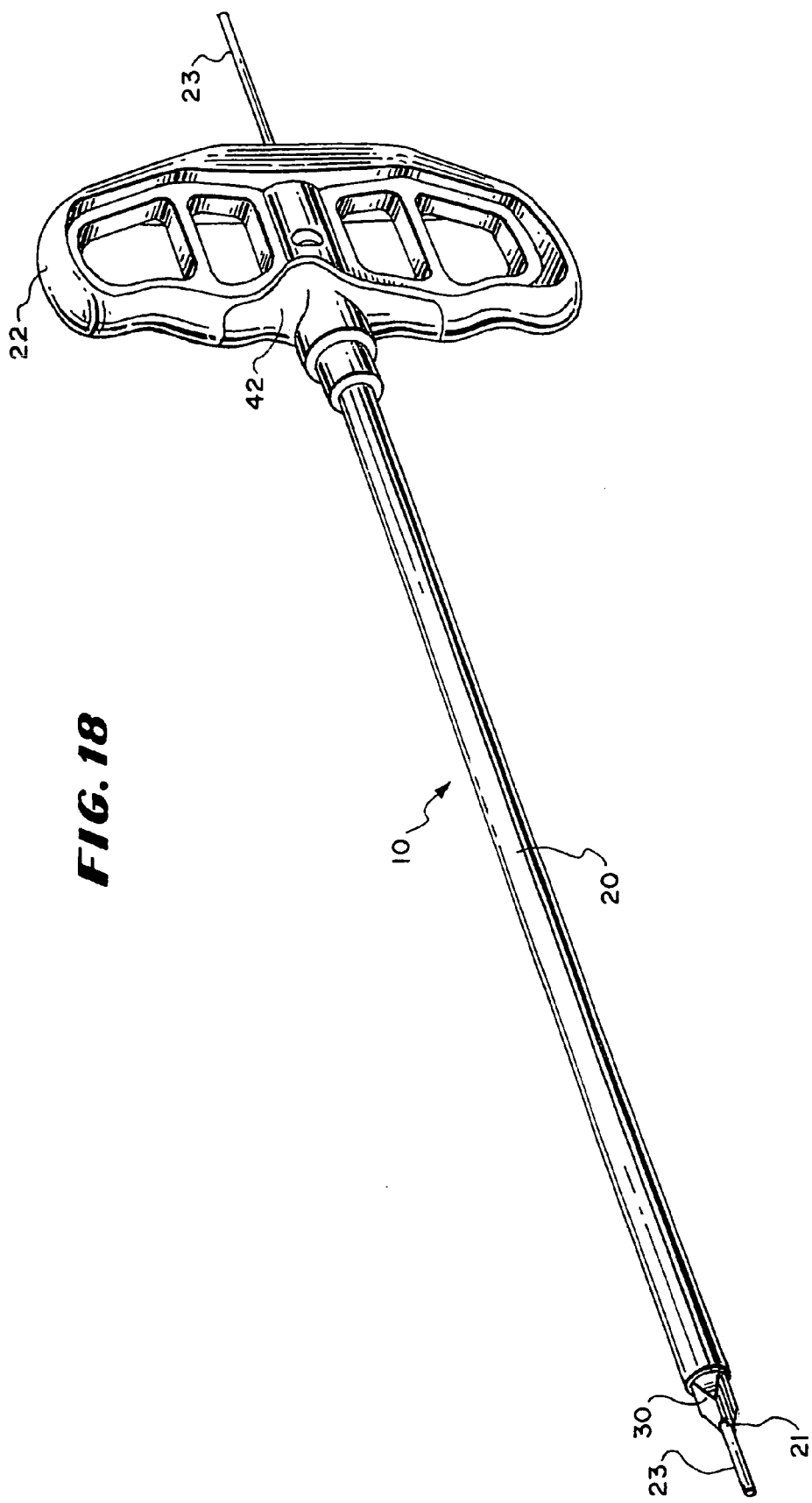
FIG. 18 a perspective view of an alternative embodiment of a composite tool like that shown in FIG. 1, with an interior lumen to accommodate passage of a spinal needle assembly to aid deployment.

In an alternative embodiment (see FIG. 18), the trocar 30 includes an interior lumen 21, which passes through the handle 22 and the body of the trocar 30. The interior lumen 21 accommodates passage of a stylet and/or conventional spinal needle assembly 23, to guide the deployment of the first instrument 20, by itself or nested with the second instrument 40 (as FIG. 18 shows), through soft tissue to a targeted bone treatment site.

B. The Cannula Instrument

The second instrument 40 functions as a cannula instrument or guide sheath, and includes a cannula 50. The cannula 50 of the second instrument 40 is desirably somewhat larger in diameter than and not as long as the trocar 30 of the first instrument 20. As best shown in FIGS. 1 and 2, the second instrument 40 includes an interior lumen 44 that extends through the instrument from its distal end 54 to its proximal end 52. The interior lumen 44 is sized to accept the trocar 30. The size of the interior lumen 44 desirably allows the second instrument 40 to slide and/or rotate relative to the first instrument 20, and vice versa, as will be described in greater detail later.

The distal end 54 of the second instrument 40 presents an end surface 60. In use, the end surface 60 of the second instrument 40 desirably presents a low-profile surface, which can penetrate soft tissue surrounding the first instrument 20 in response to pushing and/or twisting forces applied at the composite handle 12 or the second handle 42.

The proximal end 52 is coupled with the second handle 42. As best seen in FIG. 6D, the proximal end 52 of the cannula 50 desirably incorporates a flared and notched end "A" and a textured surface "B", around which the second handle 42 is molded. The flared and notched end "A" and textured surface "B" serve to increase the mechanical strength of the bond between the cannula 50 and the second handle 42, allowing significant longitudinal and torsional forces to be transmitted between the second handle 42 and cannula 50 without bond failure. As with the trocar 30, however, alternative bonding methods such as scoring of the cannula 50 and/or the use of various adhesives could be employed, with varying results.

Extending from the interior lumen 44 at the proximal end 52 of the cannula 50, the second handle 42 desirably includes a handle bore 48, preferably co-circumferential with the cannula 50. The second handle 42 includes an alignment ridge 46, and a handle groove 56, the uses of which are described later.

C. The Drill Bit Instrument

As shown in FIG. 11, an optional third functional instrument 70 functions as a drill bit. The drill bit instrument 70, having a distal end 72 and a proximal end 74, typically is slightly longer than and has generally the same physical dimensions as, the trocar 30. Like the trocar 30, the drill bit instrument 70 is intended, in use, to fit for sliding and rotational movement within the interior lumen 44 of the second instrument 40.

The distal end 72 of the drill bit instrument 70 desirably includes cutting edges 76. In use, the cutting edges 76 are intended to penetrate hard tissue in response to rotation and longitudinal load forces applied at the proximal end 74 of the drill bit instrument 70.

The drill bit instrument 70 can be of known construction, and could vary widely. Desirably, the diameter of the drill bit instrument 70 is smaller than the interior lumen 44 of the second instrument 40, and the length is longer than the cannula 50, such that the drill bit instrument 70 can access tissue deeper than the cannula 50 when the cannula 50 is installed in a patient.

II. The Instrument Handles

The first handle 22 and the second handle 42 are designed to comfortably accommodate a hand, to desirably interlock to form a composite handle 12 that resists relative rotation between the first handle 22 and the second handle 42, and desirably to indicate whether the instruments have been reused and/or resterilized.

A. Hand Accommodation

As shown in FIGS. 1–4, the composite handle 12 is shaped to be comfortably and securely grasped by a normal human hand as shown in FIG. 3. Preferably, the contours of the composite handle 12 are rounded to provide a comfortable grip and to minimize surgical glove tears.

As shown in FIG. 3, in the preferred embodiment, the first handle 22 is desirably equipped with two finger receivers 38, intended to receive the index finger and the pinkie finger of a physician.

Shown in FIG. 4, in the preferred embodiment, the second handle 42 is desirably equipped with two finger receivers 58, intended to receive the middle finger and the ring finger of a physician.

The shape and size of the first handle 22 and second handle 42, of course, vary. In the embodiment shown in FIG. 1, the composite handle 12, and in particular the first handle 22, includes a striking plate 14, elongated to fit comfortably across the palm of the hand. The striking plate 14 is also configured to receive a striking blow, described later.

B. Interlocking Configuration

Figure 5:
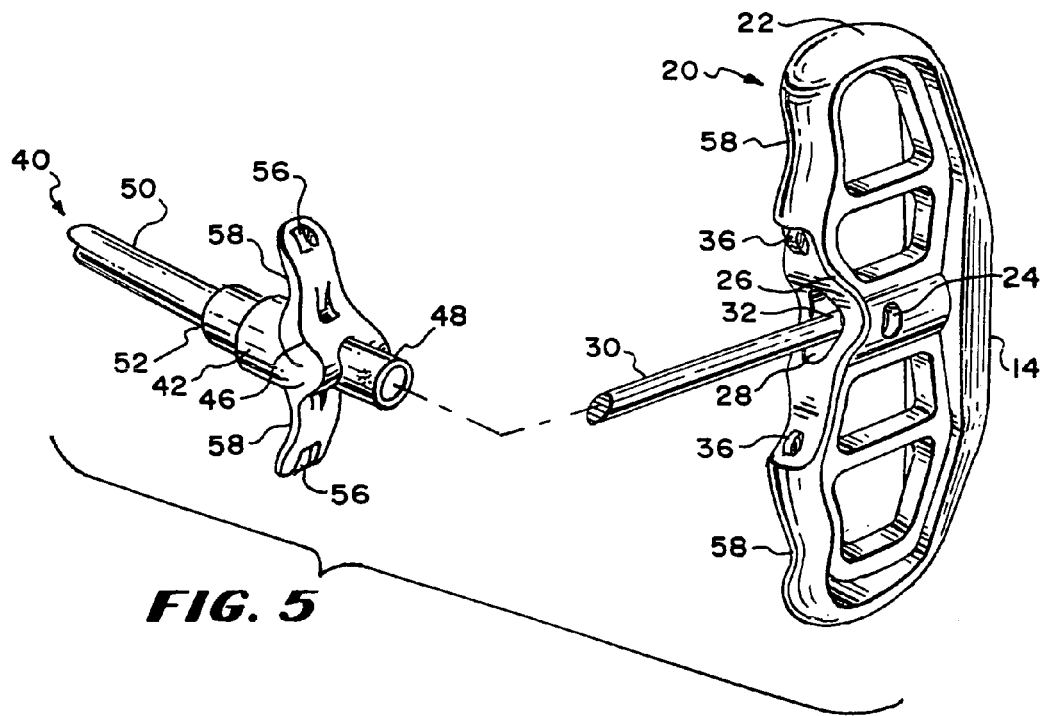
FIG. 5 is an enlarged perspective view of the handles of the first and second functional instruments, when separated, showing a coupling system than resists relative rotation between the functional instrument when the composite tool is formed.
Figure 6A:
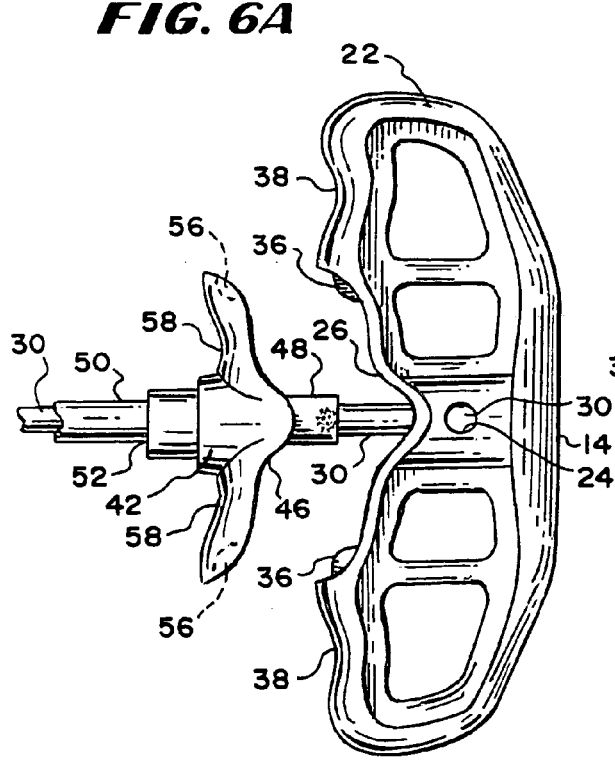
FIG. 6A is an enlarged side view of the handles shown in FIG. 5, when separated.
Figure 6B:
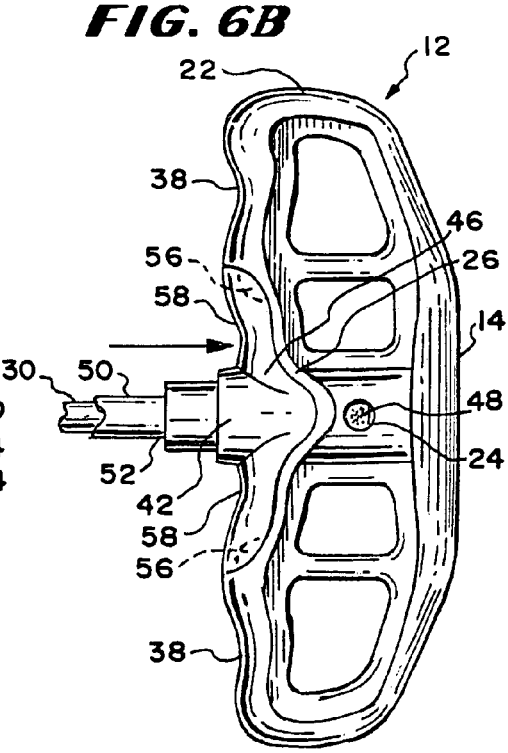
FIG. 6B is an enlarged side view of the handles shown in FIG. 5, when mated together to form the composite handle.

In order to properly interact when applying striking, pushing and/or twisting forces to the composite handle 12, the first handle 22 desirably will not rotate relative to the second handle 42. Referring now to FIGS. 5, 6A and 6B, to avoid relative rotation, the first handle 22 preferably includes the alignment ridge receiver 26 to receive the alignment ridge 46 of the second handle 42. Although described and pictured as a ridge, the alignment mechanism interaction between the first handle 22 and the second handle 42 could comprise any number of shapes other than an arcuate shape, for example a block shape or a star shape.

In use, when the trocar 30 of the first instrument 20 is slid through the cannula 50 of the second instrument 40, the first handle 22 and second handle 44 can fit together to form the composite handle 12. In addition to the alignment ridge 46 resisting rotation because of the alignment ridge receiver 26, the first handle 22 can include a handle key 36 for coupling with the handle groove 56 of the second handle 42.

If the handle groove 56 is not aligned with the handle key 36, and thus the alignment ridge 46 not aligned with the alignment ridge receiver 26, the handle bore 48 of the second handle 42 desirably will not fully insert into the handle bore receiver 28 of the first handle 22. In this alignment, the viewing window 24 will display the trocar 30, which preferably extends past the viewing window 24. Also in this alignment, the first handle 22 is desirably able to rotate independently of the second handle 42.

If, however, as shown in FIG. 6B, the handle groove 56 is aligned with the handle key 36, and thus the alignment ridge 46 is aligned with the alignment ridge receiver 26, the handle bore 48 of the second handle 42 can be fully inserted into the handle bore receiver 28 of the first handle 22.

In this operational alignment, the viewing window 24 displays the handle bore 48. Preferably, the handle bore 48 is a different color than the trocar 30 such that visualization would be simplified. Also in this alignment, the first handle 22 desirably does not rotate independently of the second handle 42. In this alignment, the composite handle 10 is sized and shaped to accommodate four fingers, two fingers each on the first handle 22 and the second handle 42.

Of course, its should be understood that the first and second handles 22 and 42 could be designed to engage in non-parallel orientations, such that the first and second handles 22 and 42 would not be parallel when properly engaged to form the composite handle 10. For example, the first handle 22 could incorporate a star or hexagonal shaped opening, into which a corresponding star or hexagonal shaped second handle 42 could engage in a multiplicity of orientations.

In use, various forces resist relative motion between the first instrument 20 and the second instrument 40. As shown in FIG. 3, when a hand grips the composite handle 10, the upward force supplied by the fingers, coupled with the downward force supplied by the palm, will compress the first instrument 20 and the second instrument 40 together. As previously noted, when properly configured, relative rotation of the instruments is desirably constrained as well.

C. Handle Materials

1. Structural Integrity

The material chosen for the first handle 22 and the second handle 42 desirably provides sufficient structural integrity to withstand manual manipulation and forces expected from manual striking blows. The first handle 22 and the second handle 42 are made from a molded or cast rigid material sufficient in strength to withstand the striking, pushing and twisting forces without significant deformation.

Another preferable characteristic of the handle composition is that the first handle 22 and the second handle 42 can be roughened or otherwise textured to provide a secure gripping surfaces.

2. Reuse

To encourage single use and discourage reuse and/or resterilization, it is preferable to differentiate between new hand tools and hand tools that have been reused and/or resterilized.

Striking and exertion of manual pressure on any of the instruments and structures described herein during first use generates stress on the material or materials which make up the instruments and/or structure. The material stress created by operational loads during first use can significantly alter the molded morphology of the structure, making future performance of the structure unpredictable.

For example, during advancement of the trocar and the cannula into the cancellous bone during a single use creates contact with surrounding cortical and cancellous bone. This contact can damage the structure, creating localized regions of weakness, which often can escape visual detection. The existence of localized regions of weakness can unpredictably cause structural failure during a subsequent use. Such contact can also cause flattening and/or curling of the end surface of the cannula, or dulling of the penetrating surface of the trocar.

In addition, exposure to blood and tissue during a single use can entrap biological components on or within the structure of the cannula or handles. Despite cleaning and subsequent sterilization, the presence of entrapped biological components can lead to unacceptable pyrogenic reactions.

As a result, following first use, the structure might not meet established performance and sterilization specifications. The effects of material stress and damage caused during a single use, coupled with the possibility of pyrogen reactions even after resterilization, reasonably justify and encourage single use for the instruments and handles that are deployed in tissue and bone.

To protect patients from the potential adverse consequences occasioned by multiple use, which include disease transmission, or material stress and instability, or decreased or unpredictable performance, various materials may be used to indicate and possibly prevent re-use and/or resterilization of the hand tools.

For example, a heat degradable material can be used to indicate, through deformation, whether a hand tool has been autoclaved. Additionally, chemical sensitive pigments, such as inks commercially available from Tempil, could be applied to the composite handle 12 to indicate, through a change of color, whether a hand tool has been chemically sterilized, for instance by use of ethylene oxide (ETO), as described in the requirements of ANSI/AAMI/ISO11135: 1994 for sterilizing devices. In addition, various materials which change color and/or physical composition in the presence of other sterilization methods, such as radiation sterilization, can be incorporated into hand tools to indicate sterilization.

Figure 17A:
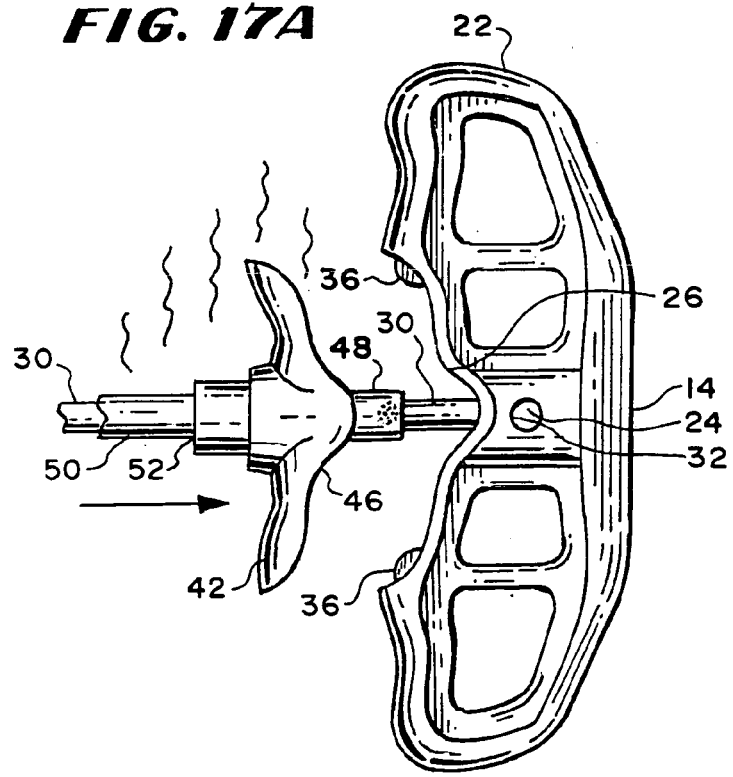
FIGS. 17A and 17B are perspective views showing material deformation that occurs in each handle as a result of heat sterilization, to prevent subsequent formation of the composite handle.
Figure 17B:
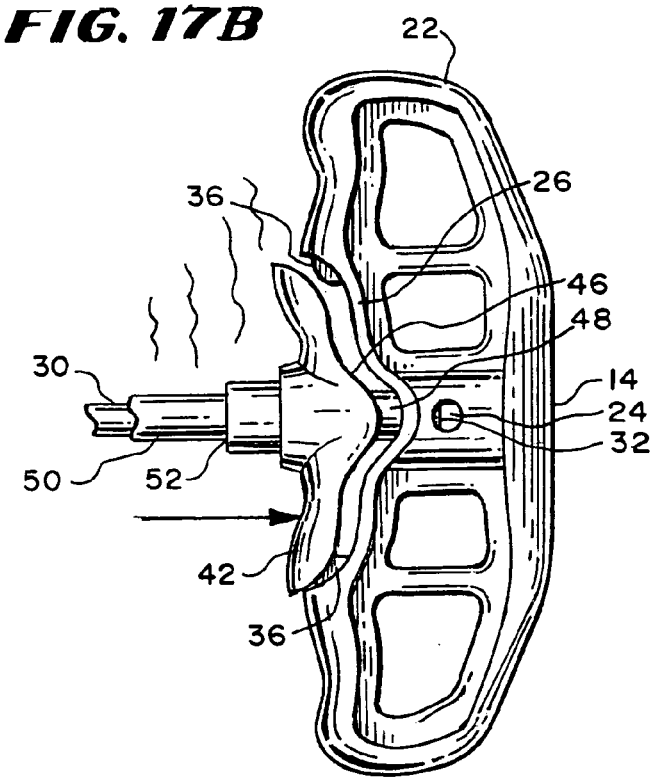

One material that provides sufficient structural rigidity and yet indicates whether an instrument has been exposed to heat common to sterilization is LUSTRAN™ material, which is commercially available from Bayer. As shown in FIGS. 17A and 17B, when this material is used in handle construction, the material will typically deform during heat sterilization, desirably preventing the handle groove 56 from aligning with the handle key 36, and thus preventing the alignment ridge 46 from aligning with the alignment ridge receiver 26. Additionally, following deformation, the handle bore 48 of the second handle 42 desirably cannot be fully inserted into the handle bore receiver 28 of the first handle 22.

III. Illustrative Use of the System

The following describes use of the composite instrument 10, instruments 20, 40, and 70, in conjunction with a catheter component 130, a diagnostic or therapeutic element 132, a syringe 136 and a tamping instrument 142 as shown in FIGS. 9–15 in the context of treating bones. This is because these items can be advantageously used for this purpose. Still, it should be appreciated that the composite instrument 10 is not limited to use in the treatment of bones, nor limited to instruments intended to contact tissue to perform a diagnostic or therapeutic function. The composite handle 12 configuration associating the first handle 22 and the second handle 42 can be used in association with various other hand-held instruments.

The composite instrument 10, handles 12, 22, and 42, and instruments 20, 40, 64 and 70 will now be described with regard to the treatment of human vertebra. It should be appreciated, however, their use is not limited to human vertebrae. The handle 18 can be used in association with hand-held instruments in the treatment of diverse human or animal bone types.

A. Vertebral Anatomy

Figure 7A:
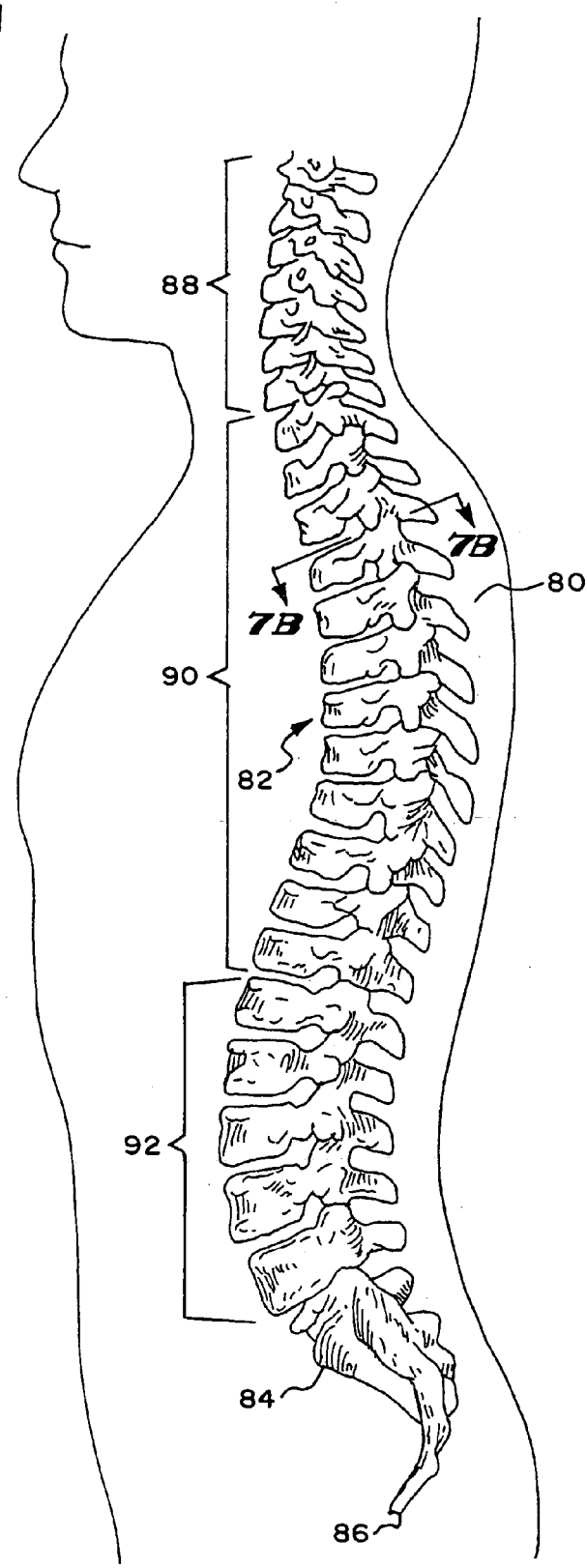
FIG. 7A is a lateral view of a human spinal column.

One use of the system is to treat vertebral bodies. As FIG. 7A shows, the spinal column 80 comprises a number of uniquely shaped bones, called the vertebrae 82, a sacrum 84, and a coccyx 86 (also called the tail bone). The number of vertebrae 82 that make up the spinal column 80 depends upon the species of animal. In a human (which FIG. 7A shows), there are twenty-four vertebrae 82, comprising seven cervical vertebrae 88, twelve thoracic vertebrae 90, and five lumbar vertebrae 92.

When viewed from the side, as FIG. 7A shows, the spinal column 80 forms an S-shaped curve. The curve serves to support the head, which is heavy. In four-footed animals, the curve of the spine is simpler.

Figure 7B:
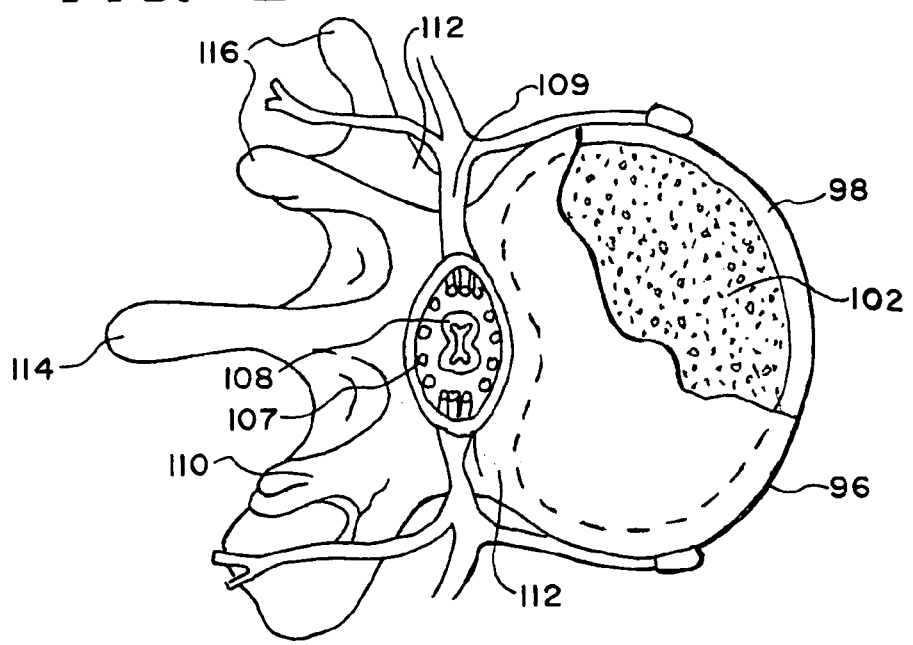
FIG. 7B is a coronal view, with portions broken away and in section, of a human vertebral body, which is part of the spinal column.
Figure 8:
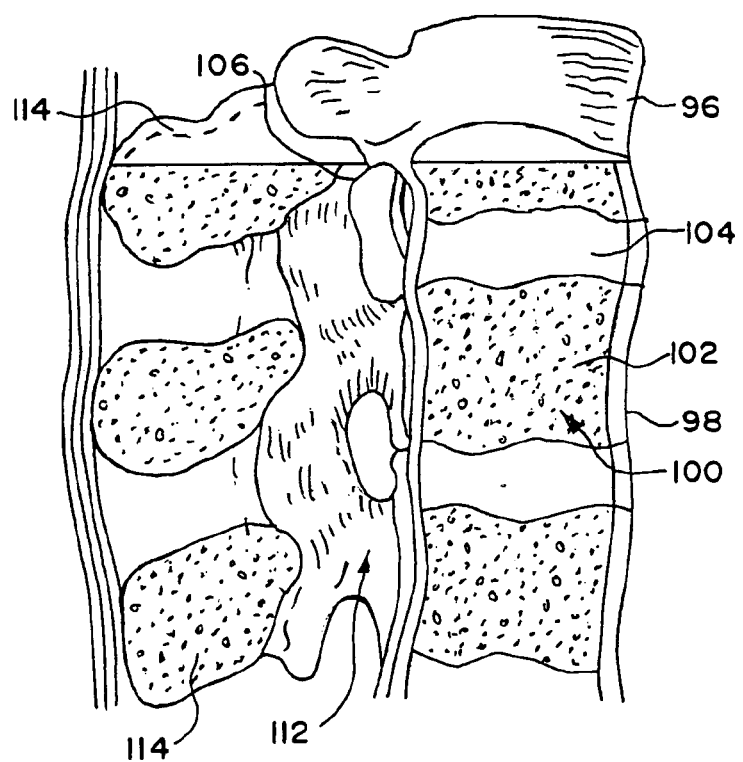
FIG. 8 is a lateral view, with portions broken away and in section, of several vertebral bodies, which are part of the spinal column.

As FIGS. 7A, 7B and 8 show, each vertebra 82 includes a vertebral body 96, which extends on the anterior (i.e., front or chest) side of the vertebra 82. As FIGS. 7A, 7B and 8 show, the vertebral body 96 is in the shape of an oval disk. As FIGS. 7B and 8 show, the vertebral body 96 includes an exterior formed from compact cortical bone 98. The cortical bone 98 encloses an interior volume 100 of reticulated cancellous, or spongy, bone 102 (also called medullary bone or trabecular bone). A "cushion," called an intervertebral disk 104, is located between adjacent vertebral bodies 96.

An opening, called the vertebral foramen 106, is located on the posterior (i.e., back) side of each vertebra 82. The spinal ganglion 109 pass through the foramen 106. The spinal cord 108 passes through the spinal canal 107.

The vertebral arch 110 surrounds the spinal canal 107. The pedicles 112 of the vertebral arch 110 adjoin the vertebral body 96. The spinous process 114 extends from the posterior of the vertebral arch 110, as do the left and right transverse processes 116.

B. Surgical Technique

In a typical procedure, a patient lies on an operating table, while the physician introduces the composite instrument 10 into soft tissue (designated S in FIG. 9) in the patient's back. The patient can lie face down on the table, or on either side, or at an oblique angle, depending upon the physician's preference. Moreover, the procedure can be performed through an open anterior procedure or an endoscopic anterior procedure.

1. Accessing Cancellous Bone

Figure 9:
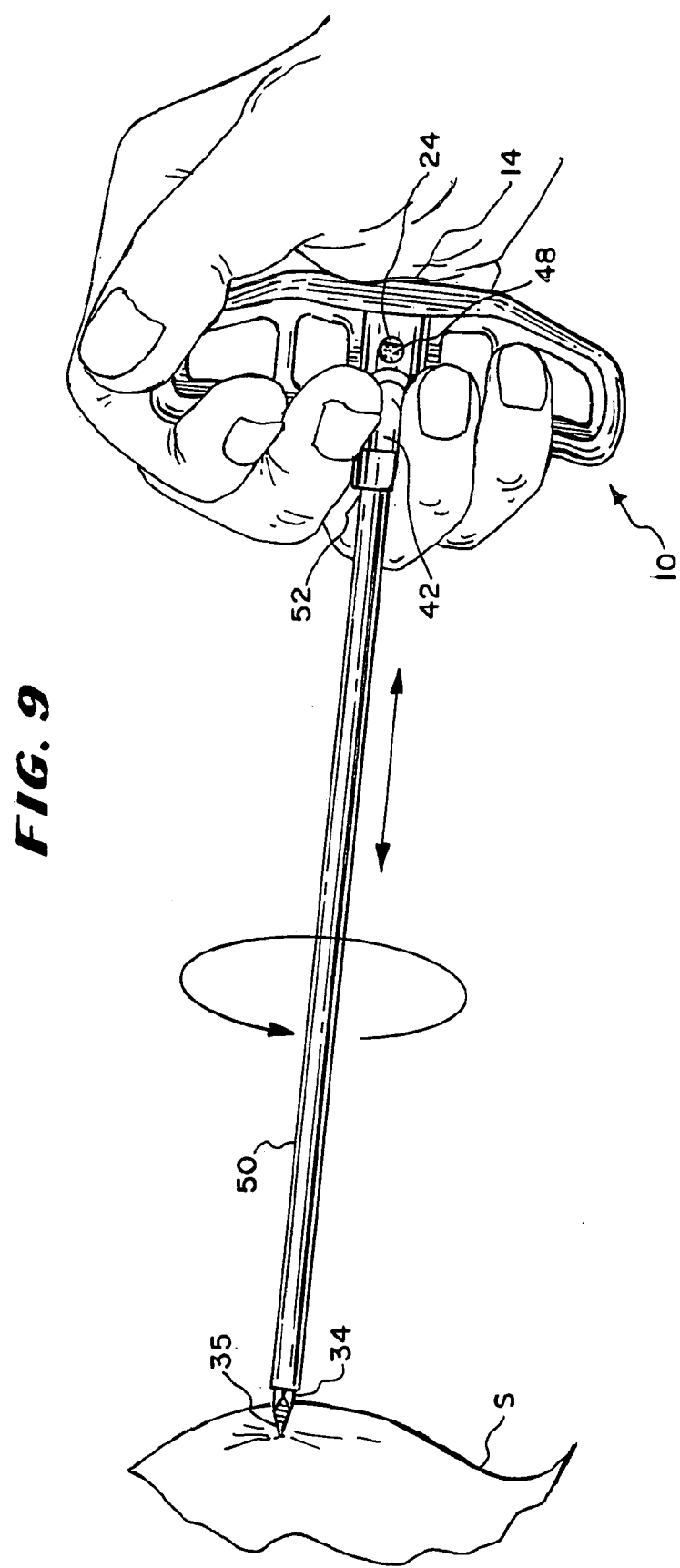
FIG. 9 is a perspective view showing advancement of the composite instrument through tissue, by using the composite handle to supply a twisting and/or pushing force.

Under radiologic or CT monitoring, the physician advances the composite instrument 10 through soft tissue S down to and into the targeted vertebra 82, as FIG. 9 shows. The physician will typically administer a local anesthetic, for example, lidocaine, to the targeted region. In some cases, the physician may prefer other forms of anesthesia, such as general anesthesia.

As shown in FIG. 10, the physician directs the composite instrument 10 such that the trocar 30 of the first instrument 20 and the cannula 50 of the second instrument 40 penetrate the cortical bone 98 and the cancellous bone 102 of the targeted vertebra 82. If desired, the physician twists the composite handle 10 while applying longitudinal force to the handle 10. In response, the penetrating surface 35 of the trocar 30, and the end surface 60 of the cannula 50 rotate and penetrate soft tissue and/or bone.

Preferably the depth of penetration of the distal end 34 of the trocar 30 and the end surface 60 of the cannula 50 are through a first wall of the cortical bone 98 and into the cancellous bone 102. However, if the penetration through the first wall of the cortical bone 98 and into the cancellous bone 102 is not achievable by manual advancement of the composite instrument 10, a physician can continue penetration by gently striking the striking plate 14 with a blunt instrument such as a surgical hammer (not shown), or otherwise applying appropriate additional longitudinal force to the composite handle 12, to advance the distal end 34 of the trocar 30 and the end surface 60 of the cannula 50.

If desired, the physician can utilize a spinal needle assembly and stylet to initially access the vertebral body 82, and then utilize the alternative embodiment shown in FIG. 18 to complete the access procedure. The embodiment shown in FIG. 18 allows the physician to place a stylet 23 into the targeted vertebral body 82, and then guide the composite instrument 10 through soft tissue and into the targeted vertebra body 82 along the stylet 23, which passes through the trocar lumen 21 as the composite instrument 10 is advanced through soft tissue and into the vertebral body 82. Once the trocar 30 has sufficiently penetrated cortical bone, the physician can withdraw the spinal needle assembly 23.

After penetrating the cortical bone 98, if desired, the physician may continue advancing the composite instrument 10 through the cancellous bone 102 of the vertebral body 96, thereby forming a passage through the cancellous bone 102. Preferably this passage will extend no more than 95% across the vertebral body. The physician may then withdraw the instrument 10, such that the cannula 50 remains within the cortical bone 98 and/or extends only part-way into the cancellous bone 102. The trocar 30 may then be withdrawn from the cannula 50, allowing access to the passage formed in the interior of the vertebral body 82 through the cannula 50.

Alternatively, after penetrating the cortical bone 98, the physician may choose to withdraw the trocar 30 from the cannula 50 and form a passage in the cancellous bone 102 using a drill bit 70. In such a case, the physician removes the first functional instrument 20 by holding the second instrument 40 in place and manually withdrawing the first instrument 20.

Next, as shown in FIG. 11, the physician advances the drill bit 70 through the cannula 50. Under X-ray control (or using another external visualizing system), the physician applies appropriate twisting and longitudinal forces to the drill bit 70, to rotate and advance the cutting edge 76 of the drill bit 70 to open a passage through the bone tissue and completely into the cancellous bone 102. The drilled passage preferably extends no more than 95% across the vertebral body 96.

At this point in the procedure, access to the cancellous bone 102 has been accomplished and the end surface 60 of the cannula 50 extends into the interior volume 100, leaving only the cannula instrument 50 in place.

2. Bone Treatment

As shown in FIG. 12, the physician can now acquire the catheter component 130. The physician can advance the diagnostic or therapeutic element 132 carried by the catheter component 130 through the handle bore 48 and cannula 50 and into the interior volume 100 of the vertebral body 96.

The distal diagnostic or therapeutic element 132 of the catheter component 130 can be configured to perform various functions. For example, the element 132 can comprise a biopsy instrument, to obtain samples of cancellous bone or to harvest bone marrow. Alternatively, the distal element 132 can be a stylet to introduce a medication or the like into cancellous bone. Still alternatively (as shown in FIG. 13), the distal element 132 can comprise an expandable body to compact cancellous bone 102 and form a cavity 134 in the vertebral body 96, in the manner disclosed in U.S. Pat. Nos. 4,969,888, 5,108,404, and 5,827,289, which are incorporated herein by reference. Upon compaction of cancellous bone 102, the distal element 132 can also include a nozzle 140 to inject a material into the formed cavity.

Figure 14:
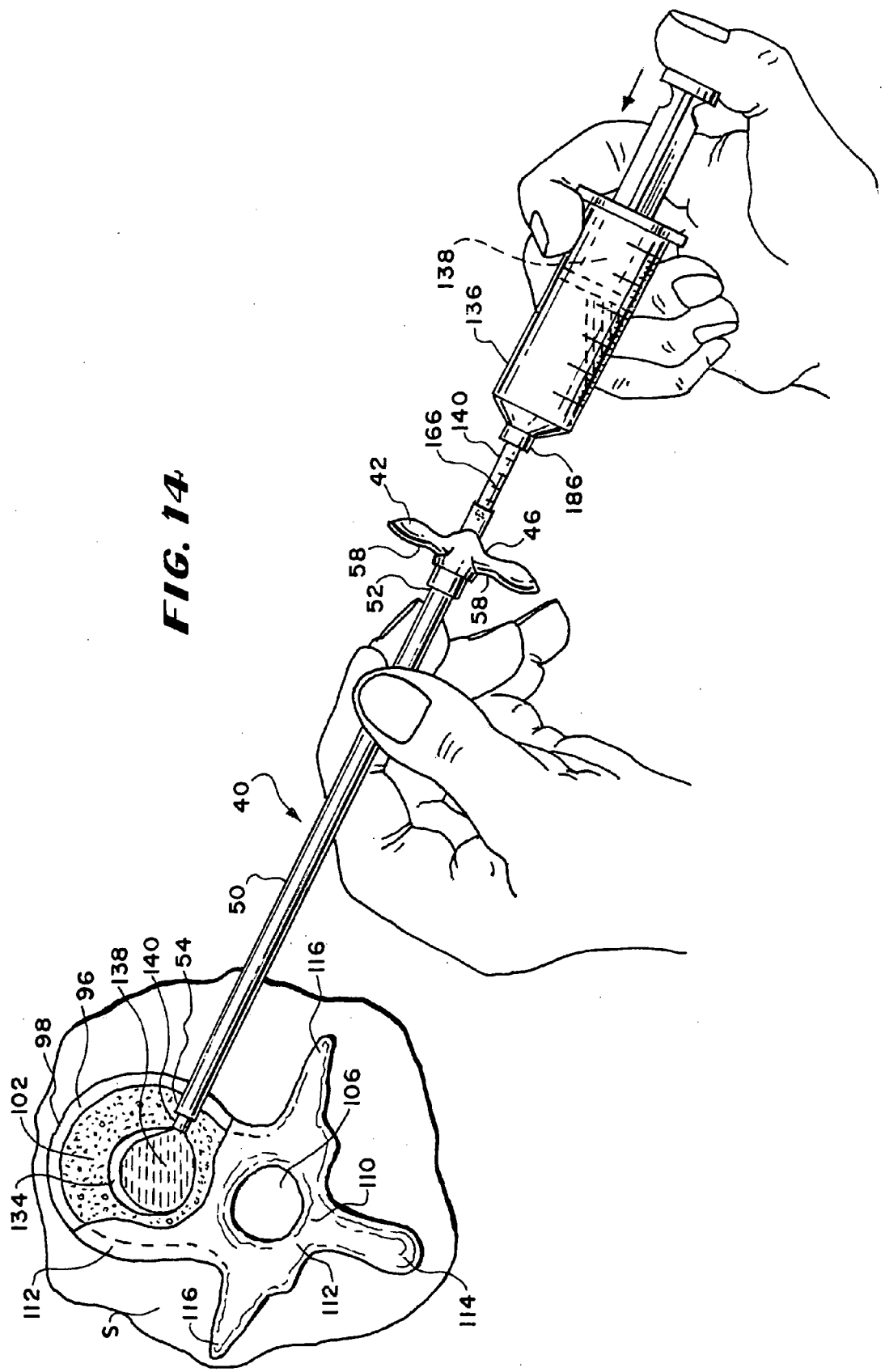
FIG. 14 is a top view of a syringe and attached nozzle in use to inject material into the cannula instrument for passage into the cavity shown in FIG. 13.

Upon formation of the cavity 134, the physician acquires a syringe 136 and injection nozzle 140. As FIG. 14 shows, the nozzle 140 is sized to pass through the cannula 50, to thereby pass into the cavity 134. The nozzle 140 connects by a threaded connector 186 to a syringe 136. The nozzle 140 can be formed from a rigid metal material, e.g., stainless steel.

As FIG. 14 shows, the physician fills the syringe 136 with the desired volume of filling material 138. The physician attaches the nozzle 140 to the filled syringe 136. The physician inserts the nozzle 140 a selected distance beyond the distal end 54 of the cannula 50 and into the cavity, guided by markings 166 on the nozzle 140. Next, the physician operates the syringe 136 to expel the material 138 through the nozzle 140 into the cavity 134.

Desirably, the physician first introduces the material 138 into the region of the cavity 134 farthest from the distal end 54 of the cannula 54. The physician successively draws the nozzle 140 toward the distal end 54 of the cannula 50, while injecting the material 138, to fill the remainder of the cavity 54.

At this stage, the nozzle 180 is unthreaded from the syringe 104. As FIG. 15 shows, the physician next advances a tamping instrument 142 through the nozzle 140. The distal end of the tamping instrument 142 contacts the residual volume of material 138 in the nozzle 140. Advancement of the tamping instrument 142 displaces the residual material 138 from the nozzle 140, forcing it into the cavity 134. The flow of material 138 into the cavity 134, propelled by the advancement of the tamping instrument 142 in the nozzle 140 serves to uniformly distribute and compact the material 138 inside the cavity 134, without the application of undue pressure.

As shown in FIG. 16, as an alternative to attaching the nozzle 140 to the syringe 136, the physician can attach the syringe 136 directly to the handle bore 48 of the second instrument 40. As shown in the alternate embodiment in FIG. 16, the syringe 136 can have threads 137 or other fasteners, such as snap-sit fasteners or luer-lock fasteners. The threads 137 would match with bore threads 49 contained in the handle bore 48. Next, the physician operates the syringe 136 to expel the material 138 through the handle bore 48 and the cannula 50 and directly into the cavity 134. In this arrangement, the physician disconnects the syringe 136 and advances the tamping instrument 142 through the handle bore 48 and the cannula 50 to displace the residual material 138 from the cannula 50, forcing it into the cavity 134.

The use of the syringe 136 with or without nozzle 140, and the tamping instrument 142 allows the physician to exert precise control when filling the cavity 134 with material 138. The physician can immediately adjust the volume and rate of delivery according to the particular local physiological conditions encountered. The application of low pressure (i.e., desirably no greater than 360 psi at the distal end of the cannula, more desirably no greater that 190 psi at the distal end of the cannula, and most desirably no greater than 100 psi at the distal end of the cannula), which is uniformly applied by the tamping instrument 142, allows the physician to respond to fill volume, flow resistance, and flow path conditions quickly. The chance of overfilling and leakage of material 138 outside the cavity portion is thereby significantly reduced.

When the physician is satisfied that the material 138 has been amply distributed inside the cavity portion, the physician withdraws the tamping instrument 142 from the cannula 50 and handle bore 48. The physician preferably first twists the tamping instrument 142 to cleanly break contact with the material 138.

Of course, this procedure could be repeated to access and treat one vertebral body multiple times in multiple orientations to create multiple cavities that may or may not interconnect. After a cavity has been filled and tamped in the above described manner, the instruments can be withdrawn and the incision sites sutured closed. The bone treatment procedure is concluded.

C. Suggested Materials

Desirably, the material 138 will provide sufficient support within the vertebral body to prevent further fracture of the body. The capability of the vertebral bodies to withstand loads will have thereby been improved. The material may also facilitate healing of the vertebral body.

The selected material 138 can be a bone cement, or autograft or allograft bone graft tissue collected in conventional ways, e.g., in paste form (see Dick, "A Use of the Acetabular Reamer to Harvest Autogenic Bone Graft Material: A Simple Method for Producing Bone Paste," *Archives of Orthopaedic and Traumatic Surgery* (1986), 105: 235–238), or in pellet form (see Bhan et al, "A Percutaneous Bone Grafting for Nonunion and Delayed Union of Fractures of the Tibial Shaft,"@ *International Orthopaedics* (*SICOT*) (1993) 17: 310–312). Alternatively, the bone graft tissue can be obtained using a Bone Graft Harvester, which is commercially available from SpineTech. Using a funnel, the paste or pellet graft tissue material is loaded into the cannula 50. The tamping instrument 142 is then advanced into the cannula 50 in the manner previously described, to displace the paste or pellet graft tissue material out of the cannula 50 and into the cavity 134.

The selected material 138 can also comprise a granular bone material harvested from coral, e.g., ProOsteon™ calcium carbonate granules, available from Interpore. The granules are loaded into the cannula 50 using a funnel and advanced into the cavity using the tamping instrument 142.

The selected material 138 can also comprise demineralized bone matrix suspended in glycerol (e.g., Grafton™ allograft material available from Osteotech), or SRS™ calcium phosphate cement available from Novian. These viscous materials, like the bone cement previously described, can be loaded into the syringe 136 and injected into the cavity directly or using the nozzle 140, which is inserted through the cannula 50 into the cavity 134. The tamping instrument 142 is used to displace residual material from the cannula 50 into the cavity 134, as before described.

The selected material 138 can also be in sheet form, e.g. Collagraft™ material made from calcium carbonate powder and collagen from bovine bone. The sheet can be rolled into a tube and loaded by hand into the cannula 50. The tamping instrument 142 is then advanced through the cannula 50, to push and compact the material in the cavity 134.

The features of the invention are set forth in the following claims.

We claim:

1. A tool system comprising
   a trocar instrument including a trocar handle with first and second finger gripping surfaces mutually sized and laterally spaced apart a first distance for gripping simultaneously by an index finger and a little finger of a hand, the trocar handle including a recess between the first and second finger gripping surfaces,
   a cannula instrument including a cannula handle with third and fourth finger gripping surfaces mutually sized and laterally spaced apart a second distance less than the first distance for gripping simultaneously by two adjacent fingers of a hand, and
   the cannula instrument including a bore sized to accommodate passage of the trocar instrument to form a composite instrument, the cannula handle nesting within the recess when the composite instrument is formed to form a composite handle comprising the first, second, third and fourth finger gripping surfaces of the trocar and cannula handles resting in an adjacent and generally coplanar relationship for gripping simultaneously the first finger gripping surface by an index finger of a hand, the second finger gripping surface by a little finger of the hand, the third finger gripping surface by a ring finger of the hand, and the fourth finger gripping surface by a middle finger of the hand, to transmit rotational and/or longitudinal forces to the composite instrument sufficient to advance the composite instrument through tissue and/or bone.

2. A tool according to claim 1
   wherein the composite handle is adapted, in use, to receive a striking force.

3. A tool system according to claim 1
   wherein the trocar handle includes a first securing element in the recess, and
   wherein the cannula handle includes a second securing element sized and configured to engage the second securing element when the composite instrument is formed to prevent independent rotation of the trocar and cannula instruments.

4. A tool system according to claim 3
   wherein at least one of the first and second securing elements includes a groove.

5. A tool system according to claim 3
   wherein at least one of the first and second securing elements includes a key for mating with a groove.

6. A surgical tool system comprising
   a first functional instrument including a first functrional handle with first and second finger gripping surfaces mutually sized and laterally spaced apart a first distance for gripping simultaneously by an index finger and a little finger of a hand, the first functional handle including a recess between the first and second finger gripping surfaces,
   a second functional instrument including a second functional handle with third and fourth finger gripping surfaces mutually sized and laterally spaced apart a second distance less than the first distance for gripping simultaneously by two adjacent fingers of a hand, and
   the second functional instrument including a bore sized to accommodate passage of the first functional instrument to form a composite instrument, the second functional handle nesting within the recess when the composite instrument is formed to form a composite handle comprising the first, second, third and fourth finger gripping surfaces of the first and second functional handles resting in an adjacent and generally coplanar relationship for gripping simultaneously the first finger gripping surface by an index finger of a hand, the second finger gripping surface by a little finger of the hand, the third finger gripping surface by a ring finger of the hand, and the fourth finger gripping surface by a middle finger of the hand, to transmit rotational and/or longitudinal forces to the composite instrument.

7. A surgical tool system according to claim 6
   wherein the first functional handle includes a first securing element in the recess, and
   wherein the second functional handle includes a second securing element sized and configured to engage the second securing element when the composite instrument is formed to prevent independent rotation of the first and second functional instruments.

8. A surgical tool system according to claim 7
   wherein at least one of the first and second securing elements includes a groove.

9. A surgical tool system according to claim 7
   wherein at least one of the first and second securing elements includes a key for mating with a groove.

* * * * *